US006919228B2

(12) United States Patent
Lian et al.

(10) Patent No.: US 6,919,228 B2
(45) Date of Patent: Jul. 19, 2005

(54) METHODS AND APPARATUS FOR THE DETECTION OF DAMAGED REGIONS ON DIELECTRIC FILM OR OTHER PORTIONS OF A DIE

(75) Inventors: Sean Lian, Allentown, PA (US); Vivian Ryan, Hampton, NJ (US); Debra Louise Yencho, Allentown, PA (US)

(73) Assignee: Agere Systems, Inc., Allentown, PA (US)

( * ) Notice: Subject to any disclaimer, the term of this patent is extended or adjusted under 35 U.S.C. 154(b) by 0 days.

(21) Appl. No.: 10/699,021

(22) Filed: Oct. 31, 2003

(65) Prior Publication Data

US 2005/0092987 A1 May 5, 2005

(51) Int. Cl.[7] .......................... H01L 21/44; H01L 21/48; H01L 21/50
(52) U.S. Cl. .......................................... 438/115; 438/15
(58) Field of Search ............................ 438/115, 14, 15; 257/48

(56) References Cited

U.S. PATENT DOCUMENTS

| 5,971,586 | A | * | 10/1999 | Mori | 700/108 |
| 6,544,862 | B1 | * | 4/2003 | Bryan | 438/455 |
| 6,736,922 | B2 | * | 5/2004 | Obregon et al. | 156/247 |
| 2003/0213614 | A1 | * | 11/2003 | Furusawa et al. | 174/256 |

* cited by examiner

*Primary Examiner*—S. V. Clark

(57) ABSTRACT

Techniques for detecting damage on an integrated circuit die using a particle suspension solution are disclosed. The particles of the suspension solution preferentially attach to damaged regions on exposed dielectric films or other portions of the die. For example, one aspect of the invention is a method of detecting damage to a dielectric film used in fabricating a die of an integrated circuit. A particle suspension solution is applied to the die and damaged regions of the dielectric film are identified as areas having an accumulation of particles of the particle suspension solution.

20 Claims, 3 Drawing Sheets

METHODS AND APPARATUS FOR THE DETECTION OF DAMAGED REGIONS ON DIELECTRIC FILM OR OTHER PORTIONS OF A DIE

FIELD OF THE INVENTION

The present invention relates generally to integrated circuits, and more particularly to detecting damage on a dielectric film or other portions of a die of an integrated circuit.

BACKGROUND OF THE INVENTION

Thin film dielectrics that are used in the fabrication of integrated circuits are often the mechanical weak link of the integrated circuit structure. Due to the emergence of conductors made from copper and insulators made from a fragile low dielectric constant (k) material, together with ultra thin silicon substrates for power-amp technologies, dielectric films are increasingly susceptible to damage during wire-bonding and die-mounting processes. Although the damage caused in these processes can be difficult to detect with standard inspections and electrical tests, it may later lead to field failures.

During packaging, the integrated circuit die is wire bonded to leads of a leadframe. A robotic bonding tool may be used in this operation. Such a tool generally includes a surface/wire-feed detection system that detects bond pads of the integrated circuit die, determines the height coordinates of the bond pads, and wire bonds the bond pads to the leadframe. After detecting the location of bond pads on the surface of the die, the bonding tool is lowered to a starting bond pad to determine the height coordinate of the pad and to adjust ultrasonic power without bonding. This first "learning touch" is performed without knowledge as to the accuracy of the height coordinate. As a result, the bonding tool frequently overestimates the distance to the height coordinate of the bond pad and the tip of the bonding tool, also referred to as a capillary/wedge, forcefully contacts the bond pad. This forceful contact may cause significant damage to the bond pad, the underlying dielectric film, and the die, and may later result in a field failure of the integrated circuit.

After an integrated circuit fails in the field, a failure mode analysis may be performed on the integrated circuit. Typically, in the process, bond wires are etched off the bond pads in order to determine if there was damage to the dielectric film during manufacturing which caused the field failure. However, the damage is difficult to detect through visual inspection alone, and due to the field failure of the integrated circuit as well as the etching of the bond wires, the integrated circuit is no longer useable.

Previous attempts to detect and prevent damage before releasing the integrated circuit for field use includes laborious inspection by operators using a microscope, as well as the reinforcement of bond pads with mechanical support structures. However, operator inspection is time consuming and expensive. Further, pad reinforcements can compromise device performance and fail to prevent damage caused by misaligned bonds. Finally, pad reinforcements are ineffective when used with bonds that have material irregularities, such as hillocks.

Thus, a need exists for a technique that detects damage to an integrated circuit resulting from the bonding process before the integrated circuit is released for field use.

SUMMARY OF THE INVENTION

The present invention in accordance with one aspect thereof provides a method of detecting damage on an integrated circuit die utilizing a particle suspension solution. The particles of the suspension solution preferentially attach to dense, fractured, or otherwise damaged regions on exposed dielectric films or other portions of a die.

For example, one aspect of the invention is a method of detecting damage on a portion of a die of an integrated circuit. A particle suspension solution is applied to the die and damaged regions of the portion of the die are identified as areas having an accumulation of particles of the particle suspension solution.

The method can be applied in an integrated circuit manufacturing process. The die may be coated with the solution after a leadframe is wire bonded to the bond pads of the die. The damaged regions may then be identified before the integrated circuit is encapsulated in packaging material. The method may also be applied in a failure mode analysis. After failure, the packaging may be removed and bond pad metal layers and wire bonds may be etched off. The solution may then be applied to the die so that damage to the dielectric may be identified.

Advantageously, the present invention provides a quick, automateable method using identifiable particles. This allows the present invention to detect fractures under the bonded area of a wire and other densification damage that is not otherwise readily observable. The accumulation of particles can be easily detected using any microscope, such as an optical microscope, a scanning electron microscope (SEM), or a fluorescent microscope. Thus, the inspections by operators using the microscope are no longer laborious. Additionally, the present invention avoids bond pad reinforcements, which compromise integrated circuit performance and are insensitive to bonds having material irregularities.

These and other objects, features, and advantages of the present invention will become apparent from the following detailed description of illustrative embodiments thereof, which is to be read in connection with the accompanying drawings.

DETAILED DESCRIPTION OF THE PREFERRED EMBODIMENTS

As will be illustrated in detail below, the present invention in an illustrative embodiment provides techniques for detecting damage on a dielectric film or other portions of a die of an integrated circuit and, more particularly, for detecting dense, fractured, or otherwise damaged regions of exposed dielectric film resulting from, for example, wire-bonding operations.

Figure 1:
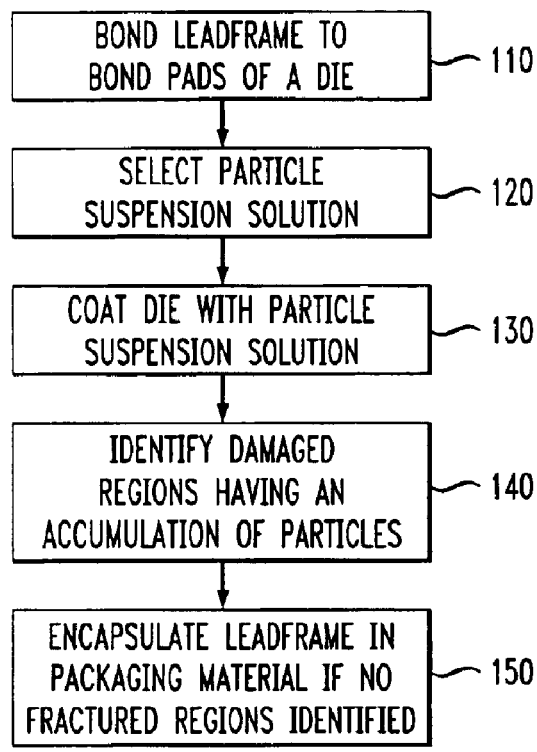
FIG. 1 is a flow diagram illustrating a damage detection methodology for integrated circuit manufacturing, according to an embodiment of the present invention.

Referring initially to FIG. 1, a flow diagram illustrates a damage detection methodology for integrated circuit manufacturing, according to an embodiment of the present invention. Integrated circuit manufacturing has many steps. The detection of damage on the dielectric may take place during the manufacturing process so that damaged integrated circuits are not sent to the field only to fail later. In the manufacturing of an integrated circuit, once the die is completed, a leadframe is bonded to the bond pads of the die through a wire-bonding process in step 110. This wire-bonding process may comprise the surface/wire-feed detection system described above. It is this wire-bonding process that may cause damage to the dielectric film of the integrated circuit, resulting in the potential for failure in the field. Therefore, an optimal time for detection of the damage is immediately after completion of the wire-bonding process.

In step 120, a particle suspension solution is selected for detecting damage on a dielectric film of an integrated circuit. The formulation and contents of the particle suspension solution are dependent on aspects of the die.

For free-standing dies, there are several types of solutions having particles suspended in an electrolyte that may be used. The purpose of the electrolyte is to exert fundamental control on attraction between the particles and surface charge groups on the dielectric film (e.g., passivation on the die, or inter-level dielectric layer under bond pad). For example, fine tungsten or copper particles can be suspended in a low to moderate concentration of phosphate buffer ($10^{-4}$ mol $dm^{-3}$ to $10^{-1}$ mol $dm^{-3}$) with a pH greater than about 3.7 in order to create the particle suspension solution. The buffer pH is preferably greater than about 3.7 so that there is a negative surface charge on the dielectric film. The buffer pH is also preferably less than about 9.0 so that the suspension remains stable. The phosphate concentration preferably allows a certain fraction of high affinity particle collisions to result in permanent contacts with the dielectric. This allows for the maximum coverage attainable for adsorbed particles on the dielectric film.

Fine positively-charged latex spheres may be substituted for the tungsten or copper particles. These colloid particles may be dyed for easier identification. Two common fluorescent dyes suitable for coating colloidal particles are rhodamine isothiocyanate-aminostyrene and 4-methylaminoethylmethacrylate-7-nitrobenzo-2-oxa-1,3-diazol.

The particles in the solution in the illustrative embodiment preferably have a surface potential which is about 10–20% greater in magnitude and of opposite sign, to the surface potential of the passivation surface. In order for any particle adsorption to occur, the surface potential of the particles are preferred to be greater than the surface potential of the dielectric film. However, at values less than 10%, the adsorption is likely reversible. The particle affinity increases as the differential increases. Therefore, between about 10% and 20%, the adsorption becomes irreversible. This range accounts for variations due to secondary effects from mechanical dislodging of larger particles. However, a surface potential greater than 20% may also work.

The distribution of particle size is preferably tight, with a mean value tailored to the dielectric film roughness. To enable a particle to contact the surface of highly textured dielectric films, the particle diameter is preferably less than the smaller value of (a) about 50% of the mean peak-to-valley height, and (b) about 50% of the mean peak-to-peak distance. Roughness values for important dielectric films commonly range from about 0.01 to 1.0 $\mu$m peak-to-valley, and from about 0.5 to 10.0 $\mu$m peak-to-peak. Therefore, in step 120, the particle suspension solution is specifically characterized in the type of particles and solution used, as well as the size, surface potential, and charge of the particles in the particle suspension solution.

In step 130, the die and its bond pads are coated with the particle suspension solution. Once coated, the particles of the solution are attracted to and accumulate on fractured, dense or otherwise damaged regions of the dielectric film. In step 140, the damaged regions of the dielectric film may be identified by finding areas having an accumulation of particles. These damaged areas may be observed with the use of an optical microscope, a scanning electron microscope (SEM), a fluorescent microscope, or other suitable mechanism. The addition of the fluorescent tags, as discussed above, makes regions having an accumulation of particles easier to identify. If there are no damaged areas, the manufacturing process of the integrated circuit continues to the final stages of manufacturing where the leadframe and die are encapsulated in packaging material in step 150 and the leads of the leadframe are cut and formed. If damaged areas are found on the dielectric film, production of the integrated circuit may not be completed.

Figure 2:
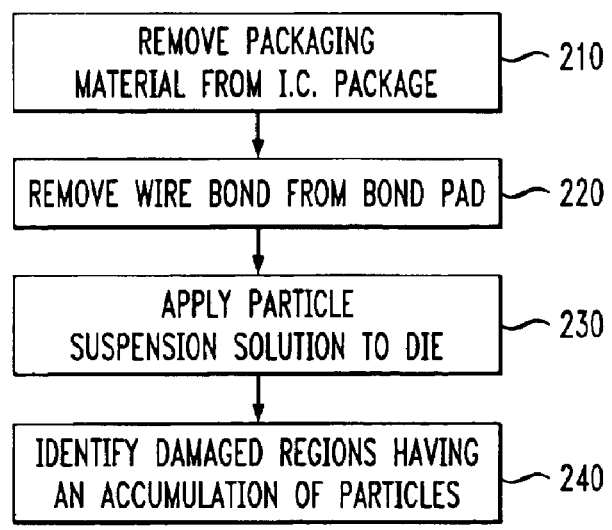
FIG. 2 is a flow diagram illustrating a damage detection methodology for failure mode analysis, according to an embodiment of the present invention.

Referring now to FIG. 2, a flow diagram illustrates a damage detection methodology for failure mode analysis, according to an embodiment of the present invention. The invention is particularly useful in failure mode analysis for integrated circuits that have failed in the field due to wire bonding damage. After an integrated circuit has failed in the field it may be analyzed to determine the reason for the failure. In step 210, the packaging material is removed from the integrated circuit package to provide access to the bond pads and the dielectric film. In step 220, the bond pad metal stacks and wire bonds are etched off or otherwise removed from the dielectric film so that the surface of the dielectric film may be examined. Bond pad etching typically utilizes wet chemistry. For example, a metal stack may comprise titanium (Ti), platinum (Pt), and gold (Au) from bottom to top. The gold bond pad is boiled in aqua regia (3 parts by volume 38% hydrochloric acid+1 part 65% nitric acid), removing the Au and Pt layers. Hydrochloric acid is then used to etch the Ti layer. If the bond pad is aluminum it is boiled in 30% each hydrochloric acid and sulphuric acid, from room temperature up to 50° C.

In step 230, the particle suspension solution is used for the detection of damage to the dielectric film of the integrated circuit. If the package contains a tungsten or copper-tungsten base plate, the particles can be generated by immersing the package in 30% hydrogen peroxide solution at 50–60° C. The particles may also be generated by immersing the package in a solution consisting of 34 grams (g) potassium dihydrogen phosphate, 13.4 g potassium hydroxide, and 33 g potassium hexacyanoferrate III, in one liter of water. The tungsten and/or copper particles of the particle suspension solution are created through the interaction of the base plate of the integrated circuit with the solution. Thus, the creation of the particle suspension solution and the application of the particle suspension solution may be achieved in the same step. Alternatively, a particle suspension solution may be selected from those solutions described in step 120 of FIG. 1. Those particle suspension solutions may then be applied to the unpackaged die. Therefore, the selection of the particle suspension solution and the application of the particle suspension solution may also be achieved in two separate steps.

In step 240, damaged regions of the dielectric surface are identified by finding the areas having an accumulation of the tungsten and/or copper particles. The accumulation of particles and the attributes of the particles are the same as described in the methodology for application during integrated circuit manufacturing as described in FIG. 1. It may then be determined whether the dielectric was damaged during the wire-bonding process and whether the damage to the dielectric was the reason for the failure in the field.

Figure 3:
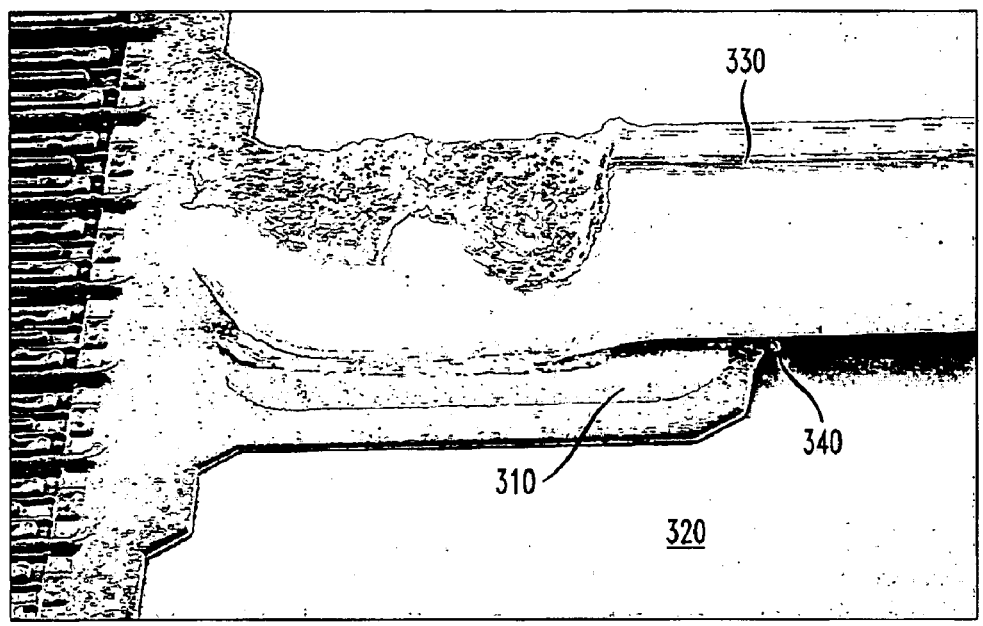
FIG. 3 is an SEM image of a wire bonded bond pad, according to an embodiment of the present invention.

Referring now to FIG. 3, an SEM image shows a wire bonded bond pad of an integrated circuit, according to an embodiment of the present invention. FIG. 3 shows the bond pad after the particle suspension solution has been applied during integrated circuit manufacturing. More specifically, this image is taken at a point in time after the wire-bonding operation of the leadframe to bond pads of the die in step 110, and after the die is coated with the particle suspension solution in step 130 of FIG. 1. A wire 330 is shown bonded to a bond pad 310 which has been coated with a dielectric film 320 of an integrated circuit, and where the dielectric film has been partially removed over the bond pad. A densification area 340 of particles of the particle suspension solution is shown under wire 330 of the wedge bond. FIG. 3 shows an example of a type of damage near a single bond pad, however in most integrated circuits there are many bond pads on the surface of the dielectric film.

Figure 4:
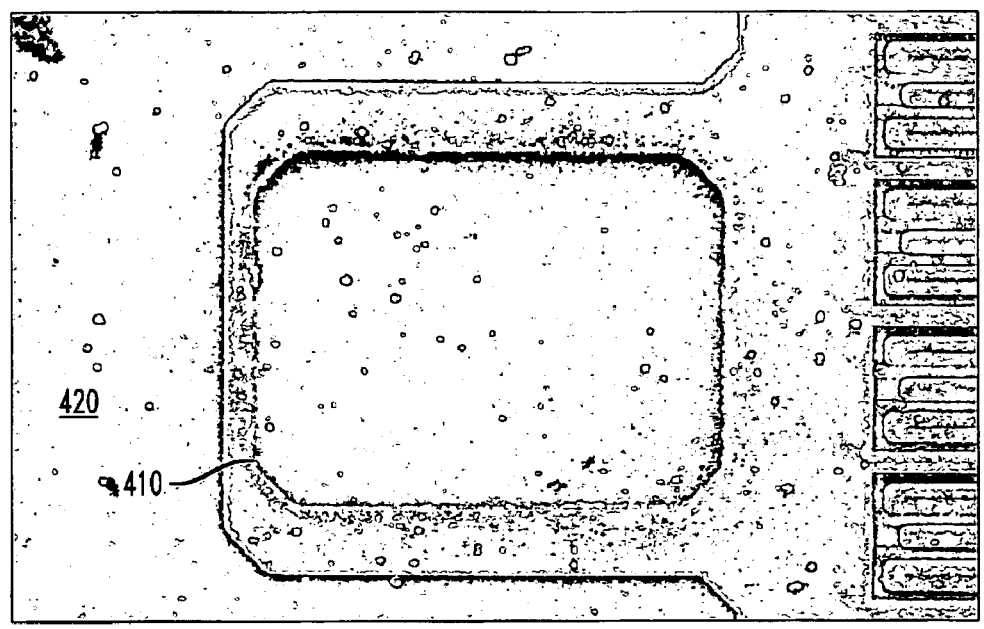
FIG. 4 is an SEM image of a dielectric film showing no damage after solution application, according to an embodiment of the present invention.

In FIG. 4, an SEM image shows a dielectric film showing no damage after solution application, according to an embodiment of the present invention. FIG. 4 shows an area of a bond pad after the particle suspension solution is applied during failure mode analysis. More specifically, this image is taken at a point in time after the bond pad metal stack and wire bonds connecting the leadframe to the die have been etched off or otherwise removed from the dielectric film in step 220, and the particle suspension solution has been applied to the die in step 230 of FIG. 2. There is no damage to the bond pad in this instance. The area of a bond pad 410 is shown on dielectric film 420 with no visible accumulation of particles. Again, FIG. 4 shows an area for a single bond pad, however in most integrated circuits there are many bond pads on the surface of the dielectric film.

Figure 5A:
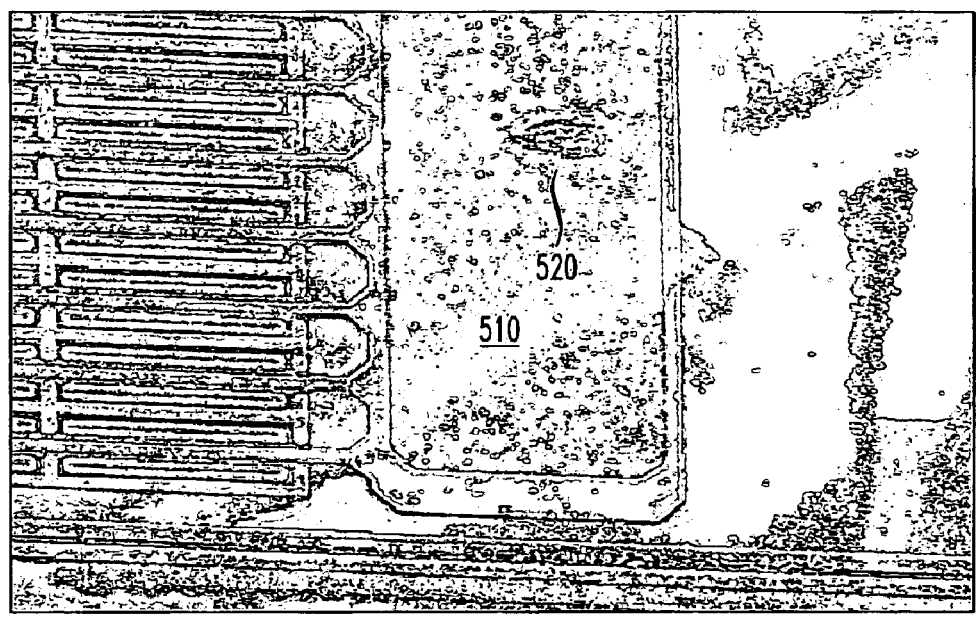
FIG. 5a is an SEM image of a dielectric film showing damage after solution application, according to an embodiment of the present invention.
Figure 5B:
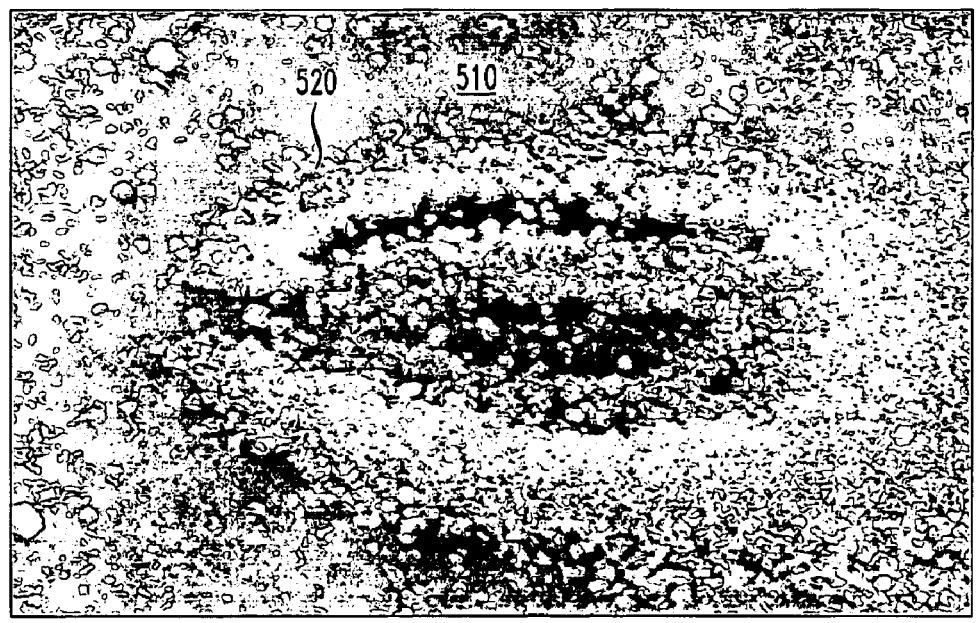
FIG. 5b is a magnified SEM image of FIG. 5a showing damage after solution application, according to an embodiment of the present invention.

Referring now to FIG. 5a, an SEM image shows a dielectric film showing damage after solution application, according to an embodiment of the present invention. FIG. 5a shows an area of a bond pad after the particle suspension solution is applied during failure mode analysis. More specifically, this image is taken at a point in time after the removal or etching off of the bond pad metal stacks and wire bonds connecting the leadframe to the die, and after the die has been coated with the particle suspension solution in step 230 of FIG. 2. Damage is shown in the densified regions, having an accumulation of particles 520 from the particle suspension solution on dielectric film 510. FIG. 5b is a magnified SEM image of FIG. 5a showing damage after solution application, according to an embodiment of the present invention.

Accordingly, as described herein, the present invention in the illustrative embodiment provides techniques for detecting damage on a dielectric film or other portions of a die of an integrated circuit. More particularly, the present invention in the illustrative embodiment provides techniques for the detection of dense, fractured, or otherwise damaged regions of exposed dielectric film resulting from, for example, wire-bonding operations.

In accordance with the embodiments of the present invention, a time period may be defined between application of the particle suspension solution and the identification of the damaged areas. This time period is determined by how long it takes for a sufficient number of particles to accumulate at damaged areas, for example, one minute. Further, regarding the embodiment described in FIG. 1, guidelines may be provided defining an accumulation of particles so that an inspector may easily determine whether a die meets a damage threshold. Regarding the embodiment described in FIG. 2, guidelines may be provided for determining whether the accumulation of particles identified by an operator mark the cause of field failure. Finally, the method and particle suspension solution of the present invention is also useful in detecting damage to metal and semiconductor films.

Although illustrative embodiments of the present invention have been described herein with reference to the accompanying drawings, it is to be understood that the invention is not limited to those precise embodiments, and that various other changes and modification may be made by one skilled in the art without departing from the scope or spirit of the invention.

What is claimed is:

1. A method for detecting damage to a portion of a die of an integrated circuit comprising the steps of:
   applying a particle suspension solution to the die; and
   identifying at least one damaged region of the portion of the die as an area having an accumulation of particles of the particle suspension solution.

2. The method of claim 1, wherein the portion of the die comprises a dielectric film of the die.

3. The method of claim 1, wherein the particle suspension solution comprises suspended particles in an electrolyte.

4. The method of claim 2, wherein the particles comprise at least one of tungsten, copper and latex spheres.

5. The method of claim 4, wherein the particles comprise latex spheres and further comprising the step of dying the latex spheres.

6. The method of claim 3, wherein the electrolyte comprises a low to moderate concentration phosphate buffer, approximately $10^{-4}$ mol dm$^{-3}$ to $10^{-1}$ mol dm$^{-3}$.

7. The method of claim 6, wherein the phosphate buffer has a pH that is greater than approximately 3.7 and less than approximately 9.0.

8. The method of claim 2, wherein a surface potential of at least one of the particles is approximately 10–20% greater than a surface potential of the dielectric film, and wherein the surface potential of at least one of the particles is opposite in sign to the surface potential of the dielectric film.

9. The method of claim 2, wherein a diameter of at least one of the particles is less than approximately 50% of a mean peak-to-valley dielectric film roughness value.

10. The method of claim 9, wherein the mean peak-to-valley dielectric film roughness value is approximately 0.01 to 1.0 μm.

11. The method of claim 2, wherein a diameter of at least one of the particles is approximately 50% of a mean peak-to-peak dielectric film roughness value.

12. The method of claim 11, wherein the peak-to-peak dielectric film roughness value is approximately 0.5 to 10.0 μm.

13. The method of claim 1, wherein the method is performed during integrated circuit manufacturing after wire bonding the die to a leadframe.

14. The method of claim 1, wherein the method is performed during failure mode analysis after removal of packaging and etching away of metal stacks and wire bonds.

15. The method of claim 1, wherein the step of applying a particle suspension solution comprises the step of immersing the die and an associated base plate in an approximately 30% hydrogen peroxide solution at approximately 50–60° C.

16. The method of claim 15, wherein tungsten particles are formed in the particle suspension solution if the base plate comprises tungsten.

17. The method of claim 15, wherein copper particles are formed in the particle suspension solution if the base plate comprises copper.

18. The method of claim 1, wherein the step of applying a particle suspension solution comprises the step of immersing the die and an associated base plate in a solution comprising potassium dihydrogen phosphate, potassium hydroxide, and potassium hexacyanoferrate III in water.

19. A particle suspension solution for detecting damage to a portion of a die of an integrated circuit, wherein the particle suspension solution is applied to the die for identifying at least one damaged region of the portion of the die as an area having an accumulation of particles of the particle suspension solution.

20. A die of an integrated circuit having a particle suspension solution applied thereto for identifying at least one damaged region of a portion of the die as an area having an accumulation of particles of the particle suspension solution.

* * * * *